United States Patent [19]
Johnson et al.

[11] Patent Number: 5,634,902
[45] Date of Patent: Jun. 3, 1997

[54] DILATATION CATHETER WITH SIDE APERTURE

[75] Inventors: Kirk L. Johnson, Miami Lakes; Pedro L. Diaz, Pembroke Pines, both of Fla.

[73] Assignee: Cordis Corporation, Miami Lakes, Fla.

[21] Appl. No.: 382,269

[22] Filed: Feb. 1, 1995

[51] Int. Cl.⁶ .................................................. A61M 29/00
[52] U.S. Cl. ........................... 604/96; 604/102; 604/282; 606/194
[58] Field of Search .................. 604/96, 95, 264, 604/280, 102, 282

[56] References Cited

U.S. PATENT DOCUMENTS

| | | | |
|---|---|---|---|
| 4,748,982 | 6/1988 | Horzewski et al. | |
| 4,762,129 | 8/1988 | Bonzel. | |
| 5,040,548 | 8/1991 | Yock. | |
| 5,156,594 | 10/1992 | Keith | 604/96 |
| 5,334,147 | 8/1994 | Johnson | 604/96 |
| 5,360,401 | 11/1994 | Turnland | 604/96 |
| 5,370,615 | 12/1994 | Johnson. | |
| 5,387,193 | 2/1995 | Miraki | 604/96 |
| 5,458,615 | 10/1995 | Klemm et al. | 604/96 X |
| B1 4,762,129 | 8/1988 | Bonzel. | |

FOREIGN PATENT DOCUMENTS 627828  8/1975  Russian Federation.

OTHER PUBLICATIONS

Brochure —Interventional Cardiology —Europass Rapid Exchange System You Pick the Size We Guarantee You'll Cross Cordis International May, 1993, 6 pages.

*Primary Examiner*—Michael Powell Buiz
*Assistant Examiner*—N. Kent Gring
*Attorney, Agent, or Firm*—Gerstman, Ellis & McMillin, Ltd.

[57] ABSTRACT

A balloon dilatation catheter defines a side aperture defined in the catheter shaft between the ends of the catheter and communicating between the guidewire lumen and the catheter exterior. A removable support mandrin may occupy a proximal lumen of the catheter. The mandrin may define a distal tip portion which is positioned preferably closely proximal to the aperture. The distal tip portion may have a reduced diameter relative to the average diameter of portions of the mandrin which are proximal to the tip portion, for providing mandrin tip flexibility. Also, a catheter-stiffening bridge member may be positioned within and permanently secured to the catheter adjacent to the aperture portion, to reduce catheter kinking adjacent thereto.

18 Claims, 1 Drawing Sheet

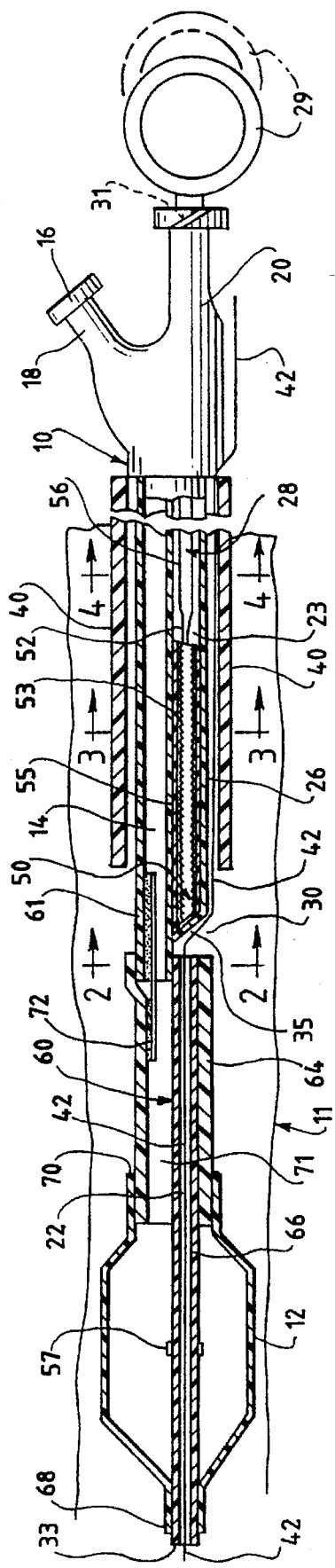
FIG. 1
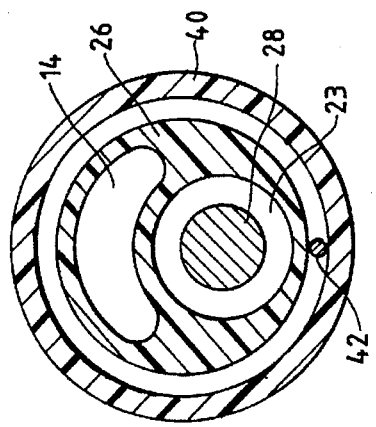
FIG. 4
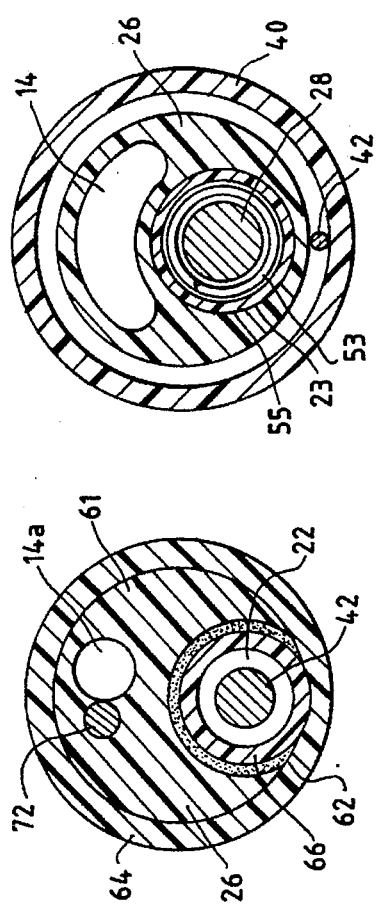
FIG. 3
FIG. 2

5,634,902

DILATATION CATHETER WITH SIDE APERTURE

BACKGROUND OF THE INVENTION

"Rapid Exchange"-type balloon dilatation catheters are catheters which are capable of advancement into the vascular system of a patient along a pre-emplaced guidewire for balloon angioplasty or the like, in which the guidewire occupies a lumen of the catheter in only a distal portion thereof. With respect to the catheter proximal portion, the guidewire exits from the internal catheter lumen and extends along the side of the catheter, being typically retained in that position by a guiding catheter in which both the catheter and the guidewire are contained. Examples of catheters of this general type include those disclosed in Horzewski et al. U.S. Pat. No. 4,748,982; Bonzel U.S. Pat. No. 4,762,129; Yock U.S. Pat. No. 5,040,548; and Johnson U.S. Pat. No. 5,334,147.

In the catheters of the above-cited patents, the distal guidewire lumens of the catheters shown have an aperture through which the guidewire can extend, so that in portions of the catheter proximal thereto the guidewire is outside of the catheter, running essentially parallel to it. By this means, the use of a guidewire extension can be avoided when exchanging catheters, providing a more rapid exchange.

A disadvantage of some of the prior "rapid exchange" type catheter systems having a lateral aperture is that the reduced length of engagement between the guidewire and catheter can compromise the handling characteristics of the catheter.

The conventional, over-the-wire mode of catheter administration lacks this disadvantage, but presents the user with a different and substantial disadvantage in that, typically, it becomes necessary to attach a catheter extension wire to the proximal end of the guidewire in order to exchange catheters without moving the guidewire out of position in the patient. However as an advantage of the over-the-wire mode, the guidewire may be quickly and easily removed and replaced without moving the catheter that surrounds it out of position.

By this invention, a catheter is provided which is capable of use in the "rapid exchange" mode of operation, but with handling characteristics that are similar to or better than those found in the conventional mode.

DESCRIPTION OF THE INVENTION

By this invention, a balloon dilatation catheter is provided having proximal and distal ends. The catheter comprises a flexible, tubular wall defining a catheter shaft, which shaft typically carries a dilatation balloon adjacent the distal catheter end. The catheter shaft typically defines an inflation lumen communicating with the balloon, plus a guidewire lumen which is separate from the inflation lumen and which extends through the catheter distal end.

A side opening aperture is defined in the catheter shaft spaced from the distal end, which aperture communicates between the guidewire lumen and the catheter exterior. In use, one may advance a catheter to pass the proximal end of a guidewire that is typically emplaced in the vascular system of the patient into the distal end of the guidewire lumen of the catheter of this invention. One may continue to advance the catheter distally along the guidewire, including the step of causing the guidewire proximal end to pass through the side aperture, so that a proximal portion of the guidewire can lie outside of and alongside the advancing catheter as the catheter is advanced. Thus the guidewire may be grasped near its proximal end as the catheter is advanced, so that the catheter may be so advanced into a patient along the emplaced guidewire without the need of a guidewire extension being attached to the guidewire proximal end.

A proximal lumen of the catheter of this invention extends proximally from the guidewire lumen and carries a removable support mandrin or stylette. This stiffens the catheter for improved performance even though the guidewire is outside of much of the catheter, thus facilitating the use of the catheter in the "rapid exchange" mode of operation. However, the support mandrin may be removable so that different mandrins may be used. Thus the catheter stiffness and the like may be adjusted for optimum performance of a single catheter in a variety of situations, just by switching of the support mandrin. Preferably, the support mandrin, when present, extends distally to essentially the side aperture. The support mandrin may have a tapered distal tip, enclosed in a support spring, to provide high tip flexibility.

Preferably, a catheter stiffening or bridge member is positioned within and permanently secured to the catheter adjacent to the aperture portion. This has the effect of reducing kinking of the catheter adjacent to the aperture portion. Typically, the bridge member is a wire positioned generally parallel to the longitudinal axis of the catheter, being preferably no more than about 10 cm. in length, so that it extends only along a minor portion of the length of the catheter, with the stiffening member fully crossing the longitudinal catheter shaft portion that defines the aperture.

The stiffening member can be secured by heat sealing or the like to the catheter, typically within the inflation lumen, with the stiffening member being adhered to and/or embedded in the wall. Also, the stiffening member may be inserted into the catheter wall during the extrusion process thereof, if desired.

In use, the catheter of this invention is typically enclosed in a guiding catheter which, in turn, is inserted into the vascular system of a patient. The dilatation catheter of this invention may be long enough to have a fully advanced position relative to the guiding catheter in which the side aperture is spaced and positioned distally forward from the guiding catheter. Thus, in an angioplasty procedure of the coronary arteries, for example, the aperture portion of the catheter of this invention may occupy a position in the coronary arteries distally forward of the guiding catheter. Particularly in this circumstance, it is preferable for the above-described stiffening member to be made of an alloy such as a superelastic nickel-titanium alloy (such as Nitinol alloy) or of an alloy having similar high elastic properties. Typically, the diameter of such a bridge member in wire form may be from about 0.006 to 0.012 inch, for example 0.009 inch, to provide to the catheter portion adjacent the side aperture a desired flexibility of bending, while at the same time preventing kinking of the catheter in use in areas adjacent to the side aperture. But for the presence of such a stiffening member, the catheter portion adjacent the side aperture would be prone to such kinking.

Alternatively, the dilatation catheter of this invention may be of such dimensions that, in its fully advanced position relative to the guiding catheter, the side aperture remains substantially positioned within the guiding catheter. In this circumstance, a stainless steel wire stiffening member may be used to provide an added amount of stiffness without the total sacrifice of flexibility to the catheter, when compared with catheters having stiffening members made of alloys such as nickel-titanium, as described above.

It is also preferable for the mandrin, in its fully advanced position in the proximal lumen, to have a distal end that is spaced no more than about 1 cm. proximally from the proximal edge of the side aperture. However, if it is desired to use the distal end of the mandrin to assist in directing the guidewire out of the aperture portion as the catheter is advanced, the mandrin distal end may be typically generally flush with the proximal edge of the side aperture.

The guidewire lumen and the proximal lumen may be separate. Alternatively, the guidewire lumen and the proximal lumen may be interconnected so that a guidewire may extend in the lumen through the entire length thereof, in conventional, over-the-wire manner.

The catheter of this invention is typically passed through a guiding catheter, typically in the "rapid exchange" mode of operation, to assure that the portion of the guidewire which passes through the side opening aperture as the catheter is advanced extends proximally from the side aperture and generally parallel to the catheter, being held in close relationship therewith by the guiding catheter.

DESCRIPTION OF DRAWINGS

In the drawings, FIG. 1 is a longitudinal, partially sectional view of a catheter in accordance with this invention, positioned in a guiding catheter;

FIG. 2 is an enlarged, sectional view taken along line 2—2 of FIG. 1;

FIG. 3 is an enlarged sectional view taken along line 3—3 of FIG. 1; and

FIG. 4 is an enlarged sectional view taken along line 4—4 of FIG. 1.

DESCRIPTION OF PREFERRED EMBODIMENT

Referring to the drawings, the proximal and distal portions of catheter 10 are shown in accordance with this invention. Catheter 10 is designed for balloon angioplasty, having a typical length of about 140 centimeters and a conventional diameter to permit entry into a small branch 11 of the coronary arteries, for angioplasty by inflation of balloon 12 by pressurizing inflation lumen 14.

Lumen 14 extends from balloon 12 to a conventional hub 16. Hub 16 has a conduit connection 18 with the inflation lumen, and a second conduit connection 20 with a separate guidewire lumen 22, which extends the entire length of the catheter, as is conventional, to provide access to both lumens.

Removable mandrin 28 is positioned in a proximal lumen 23, which is separated from guidewire lumen 22 by wall 35. Mandrin 28 can be advanced and retracted by grasping of proximal gripping ring 29. Mandrin 28 is provided for stiffening a proximal portion of the catheter during its insertion in the "rapid exchange" mode. Mandrin 28 may be removed or replaced with another, different mandrin in order to vary the stiffness and other properties of the catheter proximal portion as desired. This can be done at any time, even in the middle of a medical procedure. The mandrin may typically have a diameter of about 0.016 to 0.018 inch, specifically 0.017 inch. Also, mandrin 28 may be releasably locked in place by conventional, interrupted thread twist lock 31 or the like.

The components of catheter 10 may be typically of conventional design except as otherwise described herein.

In accordance with this invention, extruded catheter body 26 defines side aperture 30, the aperture portion communicating through the catheter wall from the guidewire lumen 22 to the exterior. Aperture 30 is typically located about 8 to 9 cm. proximally of the catheter distal tip 33.

Mandrin 28 defines a distal tip portion 50 which is positioned proximally of aperture portion 30 in the most advanced position of mandrin 28, as shown in full lines in FIG. 1. Mandrin 28 may also be withdrawn, as shown by the dotted lines adjacent to ring 29. Distal tip portion 50 defines a reduced diameter wire portion 52, which is an integral part of the rest of the mandrin wire, being typically a ground or drawn-down part of the main wire portion 56 of the mandrin 28. Reduced diameter wire portion 52 is then optionally surrounded by a coil spring 53 in the manner of known designs for guidewires, although it is to be noted that mandrin 28 of this invention is shorter than its associated catheter, while all guidewires are longer than their associated catheters.

The mandrin distal tip portion 50 may optionally be enclosed with an inner, snug-fitting flexible sleeve 55 in its fully advanced position as shown in FIG. 1, to prevent tip buckling as the mandrin tip supports wall 35. This assists in directing guidewire 42 out of side aperture 30 as catheter 10 is advanced along the guidewire.

Catheter 10 may also carry an x-ray visible marker band 57 to indicate the position of balloon 12 on a fluoroscope.

FIGS. 2–4 show cross-sections of the respective catheter lumens 14, 22, 23, the specific design of extruded catheter body 26 being as shown in Fontirroche et al. U.S. Pat. No. 5,063,018.

The distal end 33 of catheter 10 of FIG. 1 is shown projecting out of the distal end of a conventional guiding catheter 40 which, in turn, has been emplaced, along with a guidewire 42, in an artery 11. The distal portion of catheter 10, carrying balloon 12, projects outwardly from guiding catheter 40. Guidewire 42 (shown small in FIGS. 1, 3, and 4 for clarity) extends through the distal portion of catheter 10, out of aperture 30, and then proximally alongside the catheter in the conventional, rapid exchange mode. Most of that proximal portion of guidewire 42 is constrained within the bore of guiding catheter 40. Proximal lumen 23 is occupied by removable mandrel 28, in order to stiffen the catheter and to help in steering. Angled wall 35 assists in directing guidewire 42 out of aperture 30 as the catheter is advanced along the guidewire.

Catheter 10 defines a distal end section 60, which may be sealed to catheter body 26 in a manner to define side aperture 30, as shown. Catheter body 26, which extends most of the length thereof, has a distal end portion thereof 61 (FIG. 2), in which the guidewire lumen has a cutaway portion 62 formed in the wall thereof. Part of this cutaway portion 62 defines aperture 30. Aperture 30 terminates at its distal end at outer tube 64, which is sealed to the distally extending portion 61 as shown in FIG. 2. An inner tube 66 is sealed within the guidewire lumen of distal portion 61. Tube 66 is flexible but self supporting, and serves as a support and attachment site for the distal end 68 of tubular balloon 12, to provide a conventional, sealed attachment. The proximal end of tubular balloon 12 is attached to outer tube 64 at second sealing point 70.

It can be seen that outer tube 64 surrounds and encloses the distal end of inflation lumen 14, so that an intact inflation lumen 14, 71 is provided along the catheter in communication with balloon 10.

Basically, the above structure is similar to that disclosed in Johnson U.S. Pat. No. 5,370,615, modified as disclosed herein.

Further in accordance with this invention, a reinforcing and stiffening bridge wire 72 is provided, the wire 72 being sealed into strong bonding relation with the wall that defines inflation lumen 14, so that wire 72 is firmly positioned in place. Wire 72 serves to reinforce the area of the catheter which is longitudinally near side aperture 30, to eliminate or reduce catheter kinking in that area. Wire 72 longitudinally overlaps the advanced position of the distal end of mandrin 28.

Preferably, wire 72 may be sealed by a thermoforming process performed on the distal end of catheter body 26 into the desired position, and may have a diameter of about 0,009 in. and a length of about 2 in., to fully cross the longitudinal catheter shaft portion that defines aperture portion 30. The thermoforming process reshapes lumen 14 into lumen 14a, similar to the process described in Johnson U.S. Pat. No. 5,370,615, but with bridge wire 72 incorporated therein.

In this present embodiment, it can be seen that catheter 10 is long enough to permit aperture 30 to extend distally out of the guiding catheter 40. In this circumstance, the portion of dilatation catheter 10 which is distal to the guiding catheter should have a high flexibility for ease of negotiation of small coronary arteries and the like, without a tendency for kinking adjacent aperture 30. To this end, it has been found that stiffening wire 72 may be made of a superelastic nickel-titanium alloy or a similar alloy, which provides the desired characteristics of kink resistance, coupled with easy bending compliance as the catheter is advanced through the arterial system. Such alloys are commercially available under the name NITINOL, and have a very high bending resilience when compared with other alloys such as stainless steel.

However, if a catheter design is desired in which catheter 10 is proportioned so that aperture 30 does not significantly project distally out of the guiding catheter 40, then it may be desirable to use a stainless steel stiffening wire 72, or another, similar alloy, to somewhat increase the bending resistance of the catheter adjacent aperture 30 relative to the previous embodiment.

By this means, the advantages of the "rapid exchange" catheter can be achieved where that is desired, particularly the emplacement and withdrawal of catheter 10 without the need for a guidewire extension.

Catheter 10 and balloon 12 may be made of conventional plastic materials such as nylon or polyethylene terephthalate. Mandrin 28 may be made of materials such as stainless steel, platinum, nickel-titanium alloys, or combinations thereof.

The above has been offered for illustrative purposes only and is not intended to limit the scope of the invention, which is as defined in the claims below.

That which is claimed is:

1. A balloon dilatation catheter having proximal and distal ends, which comprises: a flexible, tubular wall defining a catheter shaft, which shaft carries a dilatation balloon adjacent the distal end, said catheter shaft defining an inflation lumen communicating with said balloon, a guidewire lumen extending through the catheter distal end; a side aperture defined in said catheter shaft between the ends of said catheter and communicating between said guidewire lumen and the catheter exterior; a proximal lumen extending proximally from adjacent said guidewire lumen toward the catheter proximal end; and a removable support mandrin occupying said proximal lumen, said mandrin defining a distal tip portion positioned proximally of said aperture, said distal tip portion having a reduced diameter relative to the average diameter of portions of said mandrin which are proximal to said tip portion, and a catheter stiffening bridge member being positioned within and permanently secured to said catheter shaft adjacent to said side aperture, to reduce catheter kinking adjacent to said side aperture.

2. The catheter of claim 1 in which said distal tip portion of said mandrin is surrounded by at least one of a coil spring and a flexible plastic sleeve.

3. The catheter of claim 1 having a longitudinal axis, and in which said catheter stiffening member is a wire positioned generally parallel to said axis.

4. The catheter of claim 3 in which said stiffening member is permanently secured to said catheter adjacent the inflation lumen.

5. The catheter of claim 3 in which said stiffening member is no more than about 10 cm. long, said stiffening member fully crossing the longitudinal catheter shaft portion that defines the aperture portion.

6. The dilatation catheter of claim 1, in combination with a guiding catheter in which said catheter is enclosed in said guiding catheter, said dilatation catheter having a fully advanced position relative to said guiding catheter, said side aperture being positioned distally forward from said guiding catheter when said dilatation catheter is in said fully advanced position.

7. The catheter of claim 6 in which said stiffening member is made of an alloy having the flexibility of a superelastic nickel-titanium alloy.

8. The catheter of claim 1 in which said mandrin carries a ring handle at its proximal end.

9. The catheter of claim 1 in which said mandrin is in a fully advanced position in said guidewire lumen, said mandrin having a distal end of said tip portion that substantially abuts an edge of said aperture portion.

10. A balloon dilatation catheter having proximal and distal ends, which comprises a flexible, tubular wall defining a catheter shaft, which shaft carries a dilatation balloon adjacent the distal end, said catheter shaft defining an inflation lumen communicating with said balloon and a guidewire lumen extending through the catheter distal end; a side aperture defined in a portion of said catheter shaft between the ends of said catheter and communicating between said guidewire lumen and the catheter exterior; a catheter-stiffening bridge member positioned within and secured to said catheter shaft adjacent to said side aperture to reduce catheter kinking adjacent said side aperture, said stiffening bridge member being no more than about 10 cm. long, said stiffening bridge member fully crossing the catheter shaft portion that defines the side aperture.

11. The catheter of claim 10 in which said bridge member is a wire positioned generally parallel to said axis.

12. The dilatation catheter of claim 11, in combination with a guiding catheter, in which said catheter is enclosed in said guiding catheter, said dilatation catheter being in a fully advanced position relative to said guiding catheter, said side aperture being positioned distally forward from said guiding catheter when said dilatation catheter is in said fully advanced position.

13. The catheter of claim 12 in which said stiffening member is made of superelastic nickel-titanium alloy.

14. The catheter of claim 10 in which said stiffening member is made of an alloy having the flexibility of a superelastic nickel-titanium alloy.

15. The catheter of claim 10 having a proximal lumen that extends proximally from said guidewire lumen, and a removable support mandrin occupying said proximal lumen.

16. A method of inserting a balloon dilatation catheter into the vascular system of a patient along a guidewire previously emplaced in the patient, said catheter carrying a removable mandrin in a proximal catheter lumen with the mandrin distal end being closely proximally spaced from a side aperture in said catheter, which aperture communicates between a guidewire lumen and the exterior, said method comprising: passing the proximal end of the guidewire into the distal end of a guidewire lumen of the catheter; advancing the catheter distally along the guidewire; and causing the guidewire proximal end to pass through said side opening from the guidewire lumen to the exterior as the catheter is advanced, and including the further step of removing said removable mandrin from the proximal catheter lumen and inserting another removable mandrin having different physical properties into said proximal lumen.

17. The method of claim 16 in which the distal end of said mandrin is positioned to substantially engage the guidewire proximal end as said catheter is advanced, to urge said guidewire proximal end to pass through said side opening to the exterior of the catheter.

18. The method of claim 16 in which a proximal portion of said guidewire passes through said side aperture as the catheter is advanced, and said proximal portion extends proximally from said side opening and generally parallel to said catheter, said side aperture being positioned proximally of the balloon of said catheter.

* * * * *